US012588879B2

(12) United States Patent
Nakagawa et al.

(10) Patent No.: US 12,588,879 B2
(45) Date of Patent: Mar. 31, 2026

(54) RADIATION DETECTION APPARATUS, SENSOR MODULE, AND CT APPARATUS

(71) Applicant: CANON KABUSHIKI KAISHA, Tokyo (JP)

(72) Inventors: Daiki Nakagawa, Kanagawa (JP); Yoshito Sasaki, Tokyo (JP); Tamaki Kobayashi, Kanagawa (JP); Masato Ofuji, Gunma (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 260 days.

(21) Appl. No.: 18/473,963

(22) Filed: Sep. 25, 2023

(65) Prior Publication Data

US 2024/0138787 A1 May 2, 2024

(30) Foreign Application Priority Data

Oct. 31, 2022 (JP) ................................. 2022-175026

(51) Int. Cl.
*A61B 6/42* (2024.01)
*A61B 6/03* (2006.01)
*G01T 1/20* (2006.01)

(52) U.S. Cl.
CPC ............ *A61B 6/4241* (2013.01); *A61B 6/032* (2013.01); *G01T 1/2018* (2013.01)

(58) Field of Classification Search
CPC ..... A61B 6/4241; A61B 6/032; G01T 1/2018; G01T 1/242; G01T 1/20181
See application file for complete search history.

(56) References Cited

U.S. PATENT DOCUMENTS

| | | | |
|---|---|---|---|
| 8,648,311 B2 | 2/2014 | Kobayashi | |
| 8,648,312 B2 | 2/2014 | Ichimura | |
| 8,653,465 B2 | 2/2014 | Nagano | |
| 8,704,185 B2 | 4/2014 | Ishida | |
| 8,878,972 B2 | 11/2014 | Wayama | |
| 8,957,383 B2 | 2/2015 | Sasaki | |
| 9,006,665 B2 | 4/2015 | Nagano | |
| 9,052,400 B2 | 6/2015 | Saruta | |
| 9,054,012 B2 | 6/2015 | Nomura | |
| 9,270,903 B2 | 2/2016 | Wayama | |
| 9,277,896 B2 | 3/2016 | Ofuji | |
| 9,423,513 B2 | 8/2016 | Watanabe | |
| 9,521,347 B2 | 12/2016 | Kawanabe | |
| 9,625,585 B1 | 4/2017 | Yokoyama | |

(Continued)

FOREIGN PATENT DOCUMENTS

| | | | |
|---|---|---|---|
| JP | 2010-538293 A | | 12/2010 |
| JP | 2015144746 A | * | 8/2015 |
| WO | 2009/031126 A2 | | 3/2009 |

*Primary Examiner* — Edwin C Gunberg
*Assistant Examiner* — Richard O Toohey
(74) *Attorney, Agent, or Firm* — VENABLE LLP

(57) ABSTRACT

A radiation detection apparatus includes a first sensor panel that generates a signal in accordance with incident radiation, a second sensor panel that generates a signal in accordance with incident radiation, and an adhesive member that couples together the first sensor panel and the second sensor panel. When a stimulation is applied to the adhesive member, an adhesive force of the adhesive member is lowered to a strength at which the first sensor panel and the second sensor panel can be separated without causing damage.

16 Claims, 7 Drawing Sheets

(56) References Cited

U.S. PATENT DOCUMENTS

| | | | | |
|---|---|---|---|---|
| 9,661,240 | B2 | 5/2017 | Fujiyoshi | |
| 9,675,307 | B2 | 6/2017 | Ofuji | |
| 9,726,767 | B2 | 8/2017 | Kawanabe | |
| 9,835,732 | B2 | 12/2017 | Fujiyoshi | |
| 9,838,638 | B2 | 12/2017 | Furumoto | |
| 9,948,871 | B2 | 4/2018 | Wayama | |
| 9,977,135 | B2 | 5/2018 | Yokoyama | |
| 10,068,943 | B2 | 9/2018 | Fujiyoshi | |
| 10,448,908 | B2 | 10/2019 | Sasaki | |
| 10,537,295 | B2 | 1/2020 | Watanabe | |
| 10,634,800 | B2 | 4/2020 | Yokoyama | |
| 10,741,296 | B2 | 8/2020 | Sasaki | |
| 10,914,849 | B2 | 2/2021 | Ofuji | |
| 2010/0213381 | A1 | 8/2010 | Herrmann | |
| 2023/0016138 | A1* | 1/2023 | Horiuchi | A61B 6/4266 |
| 2023/0258834 | A1 | 8/2023 | Ina | |
| 2024/0118437 | A1* | 4/2024 | Yamaji | G01T 1/20189 |

* cited by examiner

100

101

106

107

HIGH-VOLTAGE
GENERATION
APPARATUS

102

103

121

120

105

104

108 — DAS

109 — SIGNAL
PROCESSING UNIT

110 — DISPLAY UNIT

111 — CONTROL UNIT

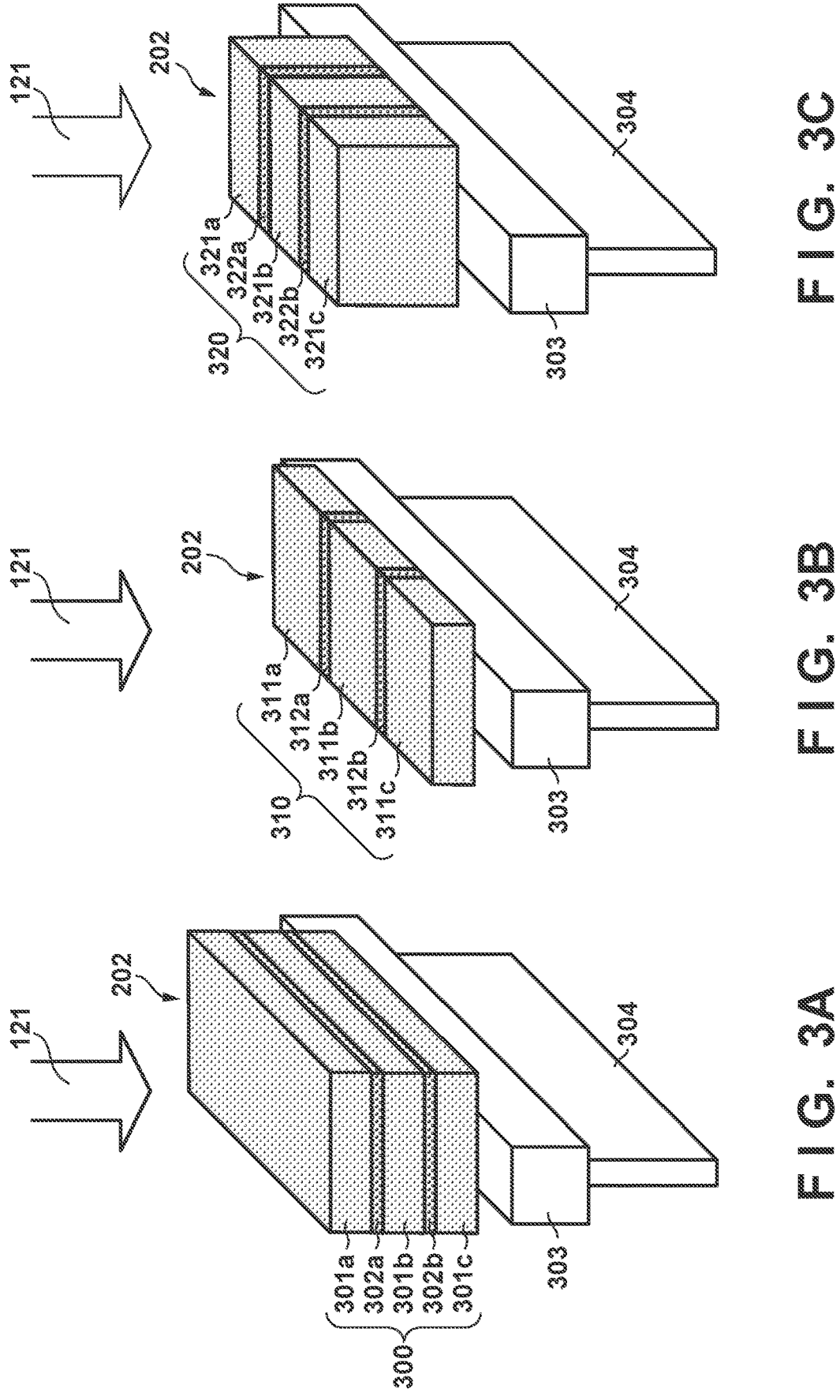
F I G. 3C
F I G. 3B
F I G. 3A

400

401
402
403
404
405
406
407

410

401
402
403
404
411
406
407

420

421
422
423
424
425
426

430

421
422
424
425
426

301a

302a

301b

301a

302a

301b

301a

302a

301b

301a

302a

301b

301a

302c

301b

301c

F I G. 7A
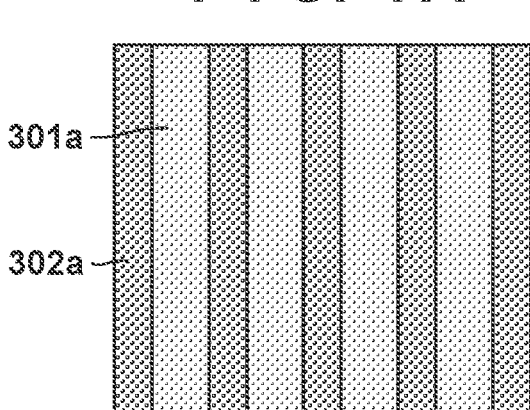
301a
302a
F I G. 7B
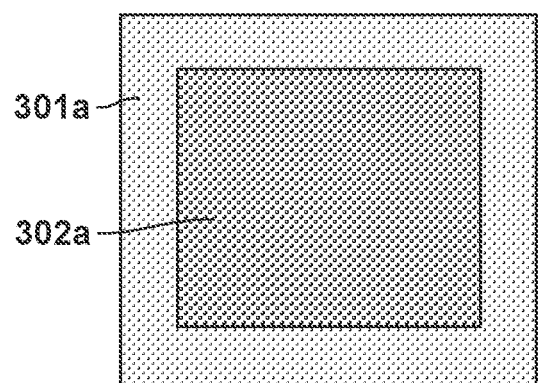
301a
302a
F I G. 7C
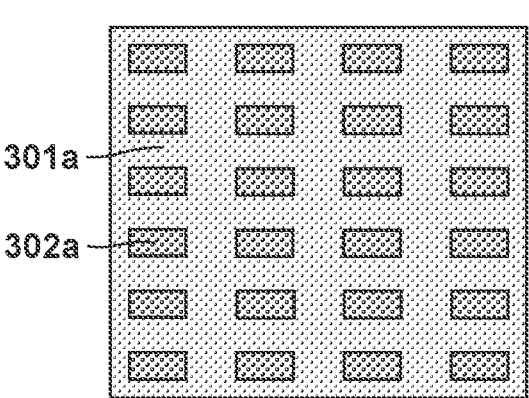
301a
302a
F I G. 7D
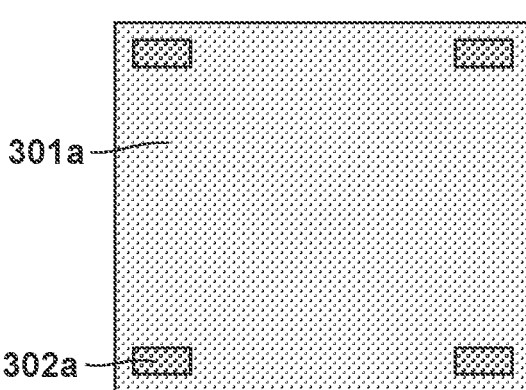
301a
302a
F I G. 7E
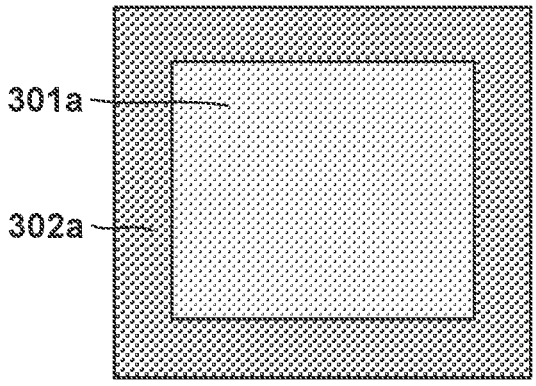
301a
302a

RADIATION DETECTION APPARATUS, SENSOR MODULE, AND CT APPARATUS

BACKGROUND OF THE INVENTION

Field of the Invention

The present disclosure relates to a radiation detection apparatus, a sensor module, and a computerized tomography (CT) apparatus.

Description of the Related Art

In the radiation detection apparatus described in Japanese Patent Laid-Open No. 2010-538293, sets of a semiconductor layer and an energy-resolving counting electronics portion are stacked in layers. With this configuration, radiation at each energy level can be detected. The radiation detection apparatus includes a plurality of sensor panels that detect radiation. When an abnormality is found in one of the sensor panels after the sensor panels are coupled together, with it being difficult to separate the sensor panels, there is a possibility that all of the sensor panels will have to be discarded. In such a case, there is a possibility that even sensor panels in which an abnormality has not been found are discarded.

SUMMARY OF THE INVENTION

An aspect of the present disclosure can easily separate a plurality of sensor panels coupled together. According to some embodiments, a radiation detection apparatus comprising: a first sensor panel that generates a signal in accordance with incident radiation; a second sensor panel that generates a signal in accordance with incident radiation; and an adhesive member that couples together the first sensor panel and the second sensor panel, wherein when a stimulation is applied to the adhesive member, an adhesive force of the adhesive member is lowered to a strength at which the first sensor panel and the second sensor panel can be separated without causing damage is provided.

Further features of the present invention will become apparent from the following description of exemplary embodiments with reference to the attached drawings.

BRIEF DESCRIPTION OF THE DRAWINGS

FIGS. 3A to 3C are perspective schematic diagrams for describing example configurations of sensor modules according to some embodiments.

FIGS. 7A to 7E are cross-sectional views for describing arrangement examples of adhesive members according to some embodiments.

DESCRIPTION OF THE EMBODIMENTS

Figure 1:
FIG. 1 is a block diagram for describing an example configuration of a CT apparatus according to some embodiments.

Hereinafter, embodiments will be described in detail with reference to the attached drawings. Note, the following embodiments are not intended to limit the scope of the claimed invention. Multiple features are described in the embodiments, but limitation is not made to an invention that requires all such features, and multiple such features may be combined as appropriate. Furthermore, in the attached drawings, the same reference numerals are given to the same or similar configurations, and redundant description thereof is omitted.

Radiation in the following description may include α-rays, β-rays, and γ-rays, which are beams of particles (including photons) emitted due to radioactive decay, as well as beams with approximately equal or greater energy, such as X-rays, a particle beam, and cosmic rays. Note that in the present application, X-ray and γ-ray photons and β-ray and α-ray particles may be collectively referred to as radiation photons.

An example of the configuration of a CT apparatus 100 according to some embodiments will be described with reference to the block diagram in FIG. 1. The CT apparatus 100 may include a radiation generator 101, a wedge 102, a collimator 103, a radiation detection apparatus 104, a top plate 105, a rotating frame 106, a high-voltage generation apparatus 107, a data acquisition system (DAS) 108, a signal processing unit 109, a display unit 110, and a control unit 111. This configuration is an example, and the CT apparatus 100 may has a different configuration.

Note that the CT apparatus 100 may be an apparatus that can execute photon counting CT. In other words, the CT apparatus 100 described in the following embodiments may be an apparatus that can reconfigure CT image data with a high SN ratio by counting the radiation photons that passes through an inspection subject using the photon counting radiation detection apparatus 104. Also, the radiation detection apparatus 104 described in the following embodiments may be a direct conversion detector that directly converts the radiation photons to a charge proportional to the energy.

The radiation generator 101 emits radiation toward the radiation detection apparatus 104. The radiation generator 101 includes a vacuum tube for generating X-rays, for example. A high voltage and a filament current is supplied from the high-voltage generation apparatus 107 to the vacuum tube of the radiation generator 101. X-rays are generated by emitting thermionic electrons from the negative electrode (filament) toward the positive electrode (target).

The wedge 102 is a filter for adjusting the amount of radiation 121 emitted from the radiation generator 101. The wedge 102 attenuates the radiation amount so that the radiation 121 emitted from the radiation generator 101 to an inspection subject 120 has a predetermined distribution. The collimator 103 includes a lead plate or the like that narrows the emission range of the radiation that passes through the wedge 102. The radiation 121 generated by the radiation generator 101 is formed into a cone beam by the collimator 103 and emitted to the inspection subject 120 on the top plate 105.

The radiation detection apparatus 104 detects the radiation 121 from the radiation generator 101 that passes through the inspection subject 120 and outputs a signal corresponding to the radiation amount to a DAS 108. The inspection subject 120 may be a living thing (for example, a human or an animal) or a non-living thing.

Note that each time a radiation photon is incident on the radiation detection apparatus 104, the radiation detection apparatus 104 may output a signal that enables the energy value of the radiation photon to be measured. The radiation photon is a radiation photon that is emitted from the radiation generator 101 and passes through the inspection subject 120, for example. The radiation detection apparatus 104 includes a plurality of detection elements that output one pulse of an electrical signal (analog signal) each time a radiation photon is incident on the detection elements. By counting the number of electrical signals (pulses), the number of radiation photons incident on the detection elements can be counted. Also, by executing arithmetic processing on the signal, the energy value of the radiation photon that has caused the output of the signal can be measured.

The detection element described above may include an electrode disposed on a semiconductor detection element made of cadmium telluride (CdTe), cadmium zinc telluride (CdZnTe), or the like. In other words, the radiation detection apparatus 104 is a direct conversion detector that directly converts incident radiation photons into electrical signals. The radiation detection apparatus 104 includes the plurality of detection elements described above and a plurality of application specific integrated circuits (ASICs) respectively connected to the detection elements that count the radiation photon detected by the detection elements. The ASICs count the number of radiation photons incident on the detection elements by discriminating between the charges output by the detection elements. Also, the ASICs measure the energy of the counted X-ray photons by executing an arithmetic processing on the basis of the magnitude of the charges. Furthermore, the ASICs output the result of counting the radiation photons to the DAS 108 as digital data.

The DAS 108 generates detection data on the basis of the result of the counting processing input from the radiation detection apparatus 104. The detection data is sinogram, for example. The sinogram is data in which the results of the counting processing for the radiation photons incident on each detection element at each position of the radiation generator 101 are arranged. The sinogram is data in which the results of the counting processing are arranged in a two-dimensional cartesian coordinate system with view direction and channel direction as the axes. The DAS 108 generates a sinogram per column in the slice direction of the radiation detection apparatus 104, for example. The result of the counting processing is data in which the number of photons of radiations per energy bin is allocated. For example, the DAS 108 counts the photons (radiation photons) resulting from the radiation that is emitted from the radiation generator 101 and passes through the inspection subject 120 and discriminating between the energy levels of the counted radiation photons to obtain the counting processing result. The DAS 108 is implemented by a processor, for example.

The rotating frame 106 has an annular shape and can rotate. Inside the rotating frame 106, the radiation generator 101 (the wedge 102 and the collimator 103) and the radiation detection apparatus 104 are disposed on opposite sides relative to the top plate 105. The radiation generator 101 and the radiation detection apparatus 104 can rotate together with the rotating frame 106.

The high-voltage generation apparatus 107 includes a boost circuit and outputs a high voltage to the radiation generator 101. For example, the high-voltage generation apparatus 107 includes an electric circuit such as a transformer, a rectifier, or the like; a high-voltage generator that generates a high voltage to be applied to the radiation generator 101; and a radiation control unit that controls the output voltage in accordance with the radiation generated by the radiation generator 101. The high-voltage generator may be a transformer type or an inverter type of generator. The high-voltage generation apparatus 107 may be provided on the rotating frame 106 or may be provided on a not-illustrated fixed frame. The DAS 108 includes an analog/digital (A/D) conversion circuit and outputs a signal from the radiation detection apparatus 104 to the signal processing unit 109 as digital data.

The signal processing unit 109 processes the signal output from the radiation detection apparatus 104. The signal processing unit 109 may include a central processing unit (CPU), a read-only memory (ROM), and a random-access memory (RAM). The display unit 110 includes a flat display apparatus or the like and can display radiation images. The control unit 111 includes a CPU, a ROM, a RAM, and the like and controls the operations of the entire CT apparatus 100. For example, the control unit 111 includes a processing circuit with a CPU and the like and a driving mechanism such as a motor, an actuator, or the like. The control unit 111 receives input signal from an input interface and performs operation control of the gantry and the couch. For example, the control unit 111 controls the rotation of the rotating frame 106, the tilt of the gantry, and operations of the couch and the top plate, and the like. For example, the control unit 111, as an example of control to tilt the gantry, rotates the rotating frame 106 about an axis parallel with the X-axis direction on the basis of the input inclination angle (tilt). Note that the control unit 111 may be provided in the gantry or may be provided in a console apparatus.

The input interface accepts various types of input operations from an operator, converts the accepted input operation to an electrical signal, and outputs the electrical signal to the control unit 111. Also, for example, the input interface accepts, from an operator, an input operation such as a reconfigure condition for when reconfiguring the CT image data, an image processing condition for when generating a post-processing image from the CT image data, and the like. For example, the input interface is implemented by a mouse and keyboard, a trackball, a switch, a button, a joystick, a touchpad where input operations are performed by touching the operation surface, a touch screen including a display screen and a touchpad integrally formed, a non-contact input circuit using an optical sensor, an audio input circuit, or the like. The input interface may be provided in the gantry. Also, the input interface may include a tablet terminal or the like that can wirelessly communicate with the console apparatus body. Also, the input interface is not only limited to including physical operation components such as a mouse and keyboard. For example, another example of the input interface includes an electrical signal processing circuit that receives an electrical signal corresponding to an input operation from an external input device provided separately to the console apparatus and outputs the electrical signal to the control unit 111.

The signal processing unit 109 may include a preprocessing function. The signal processing unit 109 with the preprocessing function executes logarithmic conversion processing and offset correction processing, inter-channel sensitivity correction processing, beam hardening correction, and other similar preprocessing on the detection data output from the DAS 108 to generate projection data. Also, the signal processing unit 109 may include a reconfigure processing function. The signal processing unit 109 with the reconfigure processing function executes reconfigure processing using a filter correction back projection method, a successive approximation reconfiguration method, or the like on the projection data generated by the preprocessing function to generate CT image data. Also, the signal processing unit 109, with the reconfigure processing function, can store the reconfigured CT image data in the memory.

The projection data generated from the counting results obtained via photon counting CT includes information relating to the energy of X-rays attenuated by passing through the inspection subject 120. Thus, the signal processing unit 109 can reconfigure the CT image data of a specific energy component via the reconfigure processing function, for example. Also, the signal processing unit 109 can reconfigure the CT image data of each energy component via the reconfigure processing function, for example. Also, for example, the signal processing unit 109, with the reconfigure processing function, can allocate the color tone in accordance with the energy component to each pixel of the CT image data for each energy component and generate image data superimposed with a plurality of pieces of CT image data colored according to the energy components. Also, for example, the signal processing unit 109, with the reconfigure processing function, can generate image data that enables a substance to be identified by using the K-absorption edge inherent to the substance. Examples of other image data generated by the reconfigure processing function of the signal processing unit 109 include monochromatic X-ray image data, density image data, effective atomic number image data, and the like.

To reconfigure CT image data, projection data covering the full circumference, that is, 360 degrees, of the inspection subject or projection data covering 180 degrees plus a fan angle, in the case of a half scan method, is required. Any reconfiguration method is applicable to the present embodiment. For ease of description, in the examples described below, a reconfiguration (full scan reconfiguration) method is used in which reconfiguration is performed using projection data covering the full circumference, that is, 360 degrees, of the inspection subject.

The signal processing unit 109 may include an image processing function. The signal processing unit 109 with the image processing function can, on the basis of an input operation accepted from an operator via the input interface, convert the CT image data generated by the reconfigure processing function, using a known method, into image data such as a tomogram of a discretionary cross section and a three-dimensional image obtained via rendering processing. Also, the signal processing unit 109, with the image processing function, can store the converted image data in the memory.

The control unit 111 may include a scan control function. The control unit 111 with the scan control function controls the CT scan performed using the gantry. For example, the control unit 111, with the scan control function, controls the operations of the high-voltage generation apparatus 107, the radiation detection apparatus 104, the DAS 108, and a couch drive apparatus to control the acquiring processing for the counting results in the gantry. For example, the control unit 111, with the scan control function, controls acquiring processing of projection data for both imaging to acquire positioning images (scan images) and actual imaging (scanning) to acquire an image to use in diagnosis. Also, the control unit 111 may include a display control function. The control unit 111, with the display control function, can perform control to display the various types of image data stored by the memory on a display such as the display unit 110.

Figure 2:
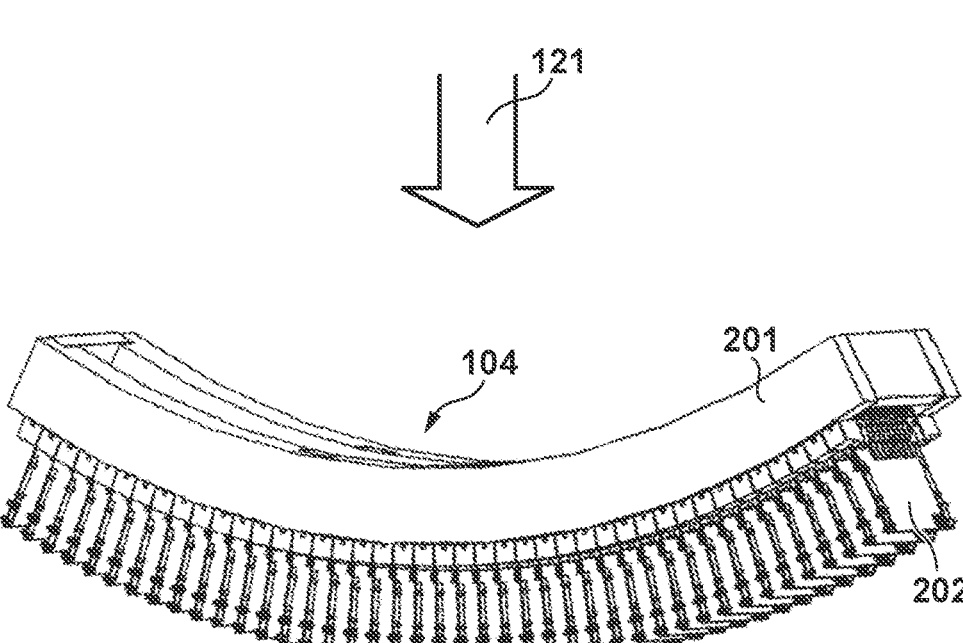
FIG. 2 is a perspective view for describing an example configuration of a radiation detection apparatus according to some embodiments.

An example of the configuration of the radiation detection apparatus 104 will now be described with reference to the perspective view of FIG. 2. This configuration is an example, and the radiation detection apparatus 104 may has a different configuration. The radiation detection apparatus 104 includes a base 201 and a plurality of sensor modules 202. The base 201 has an arc shape recessed with respect to the radiation 121. The plurality of sensor modules 202 are arranged in the circumferential direction and fixed to the curved surface of the base 201. The base 201 is fixed to the rotating frame 106.

Examples of configurations of the sensor modules 202 will now be described with reference to the perspective views of FIGS. 3A to 3C. These configurations are examples, and the sensor modules 202 may have a different configuration. The plurality of sensor modules 202 included in the radiation detection apparatus 104 may all have one of the configurations described using FIGS. 3A to 3C. In the example illustrated in FIG. 3A, the sensor module 202 may include a sensor unit 300, a frame 303, and a circuit board 304. The sensor unit 300 may include a plurality of sensor panels 301a to 301c and a plurality of adhesive members 302a and 302b. Hereinafter, the plurality of sensor panels 301a to 301c are referred to by the generic term sensor panel 301. The description of the sensor panel 301 may be applied to each one of the plurality of sensor panels 301a to 301c. Also, the adhesive members 302a and 302b are referred to by the generic term adhesive member 302. The description of the adhesive member 302 may be applied to each one of the plurality of adhesive members 302a and 302b. In the example in FIG. 3A, one sensor module 202 includes three sensor panels 301, but the number of sensor panels is to limited by this example. Also, one sensor module 202 may include a plurality of the sensor units 300. Hereinafter, the surface of each member on the upper side of the paper is referred to as the upper surface, and the surface on the lower side of the paper is referred to the lower surface.

The plurality of sensor panels 301a to 301c each generate a signal in accordance with incident radiation. The plurality of sensor panels 301a to 301c are layered on one another with respect to the radiation 121. The plurality of sensor panels 301a to 301c being layered on one another with respect to the radiation 121 means that the plurality of sensor panels 301a to 301c overlap in the direction from the radiation generator 101 toward the radiation detection apparatus 104. Hereinafter, the direction from the radiation generator 101 toward the radiation detection apparatus 104 is referred to as the advancement direction of the radiation 121. The plurality of sensor panels 301a to 301c are arranged in a direction (downward direction in the diagrams) from the radiation generator 101 toward the radiation detection apparatus 104. As described below, the sensor panel 301 may include a plurality of pixels arranged along a flat surface (for example, the upper surface of the sensor panel 301) orthogonal to the advancement direction of the radiation 121.

The adhesive member 302a is located between the sensor panel 301a and the sensor panel 301b. The adhesive member 302a is in contact with both the lower surface of the sensor panel 301a and the upper surface of the sensor panel 301b and thus couples together the sensor panels. The adhesive member 302b is located between the sensor panel 301b and the sensor panel 301c. The adhesive member 302b is in contact with both the lower surface of the sensor panel 301b and the upper surface of the sensor panel 301c and thus couples together the sensor panels. The thickness of the sensor panel 301 may range from 1.7 mm to 6.6 mm, for example. The thickness of the adhesive member 302 may range from 0.01 mm to 10 mm, for example.

Of the plurality of sensor panels 301a to 301c, the sensor panel 301a is located closest to the radiation generator 101 and the sensor panel 301c is located farthest from the radiation generator 101. Of the radiation 121 incident on the radiation detection apparatus 104, the component with a low energy level is converted into a signal at the sensor panel 301a. Of the radiation 121, the component with a moderate energy level passes through the sensor panel 301a and is converted into a signal at the sensor panel 301b. Of the radiation 121, the component with a high energy level passes through the sensor panel 301a and the sensor panel 301b and is converted into a signal at the sensor panel 301c. The sensor panel 301 and the circuit board 304 are connected by a (non-illustrated) cable (flexible cable, for example). The signal generated at the sensor panel 301 is read out to the DAS 108 via the circuit board 304.

The frame 303 is a member with sufficient rigidity so that the sensor unit 300 can be attached. The frame 303 may be referred to as a mount frame. The frame 303 may be made of metal, for example. The frame 303 functions as a support member for supporting the sensor unit 300. The sensor unit 300 may be mechanically fixed to the frame 303 using a fastener such as a machine screw or the like. The circuit board 304 is attached to the frame 303. The sensor unit 300 and the circuit board 304 are located on opposite sides relative to the frame 303. The frame 303 is fixed to the base 201. For example, the frame 303 may be mechanical fixed to the base 201 using a fastener such as a machine screw or the like.

Hereinafter, the adhesive member 302a that couples together the sensor panel 301a and the sensor panel 301b will be described. However, a similar description can be applied to the adhesive member 302b that couples together the sensor panel 301b and the sensor panel 301c. Also, when the radiation detection apparatus 104 includes four or more sensor panels, a similar description can be applied to the adhesive members that couple together these sensor panels 301.

When a specific stimulation is not applied to the adhesive member 302a, the adhesive member 302a has the adhesive force of a strength sufficient to retain the couple between the sensor panel 301a and the sensor panel 301b when the radiation detection apparatus 104 is in use. When a specific stimulation is applied to the adhesive member 302a, the adhesive force of the adhesive member 302a is lowered to a strength at which the sensor panel 301a and the sensor panel 301b can be separated without causing damage. By the adhesive member 302a having such characteristics, when an abnormality occurs in only one of the sensor panel 301a and the sensor panel 301b, repair or replacement can be performed only for that one. The sensor panel without an abnormality can be reused.

Take an example in which an abnormality is found in one of the sensor panels 301 (in this example, the sensor panel 301a, for example) by an inspection after the manufacture of the sensor modules 202, or an inspection after the manufacture of the radiation detection apparatus 104, and when actually used. In this case, the repair worker first detaches the sensor unit 300 from the frame 303. Thereafter, the repair worker lowers the adhesive force of the adhesive member 302a by applying the specific stimulation to the adhesive member 302a. Thereafter, the repair worker detaches the sensor panel 301a, couples a new sensor panel 301 to the sensor panel 301b using a new adhesive member 302, and attaches the assembly to the frame 303. The abnormality of the sensor module 202 is resolved in this manner. The normally functioning sensor panel 301b and the sensor panel 301c of the sensor module 202 are reused.

The specific stimulation for lowering the adhesive force of the adhesive member 302a may include at least one of heating, adding water, dropping a solution, and photostimulation. Also, the specific stimulation for lowering the adhesive force of the adhesive member 302a may include applying a tensile force. The adhesive member 302a may be a sheet-like adhesive member, a coatable adhesive member, or another type of adhesive member.

Examples of a substance for lowering the adhesive force via heating include a generic plastic such as polyethylene or polypropylene and an engineering plastic such as polyamide and polycarbonate. Other examples of a substance for lowering the adhesive force via heating include ammonium carbonate, ammonium hydrogen carbonate, sodium hydrogen carbonate, ammonium nitrite, and sodium tetrahydroborate. Yet more examples of a substance for lowering the adhesive force via heating include inorganic foaming agents such as azides, azo compounds, N-nitroso compounds, other low-boiling-point compounds, and rubber-based substances. When lowering the adhesive force of the adhesive member 302a via heating, the repair worker may heat the entire sensor unit 300 using a hot plate or may locally heat the adhesive member 302a using a hot gun.

The temperature for lowering the adhesive force of the adhesive member 302a may be lower than the heat-resistant temperature of the sensor panel 301. For example, the heat-resistant temperature of the sensor panel 301 may be 100° C. In this case, the temperature for lowering the adhesive force of the adhesive member 302a may be a temperature less than 100° C. such as 80° C. or less, for example. The temperature for lowering the adhesive force of the adhesive member 302a may be higher than the maximum temperature that the adhesive member 302a is expected to receive when the radiation detection apparatus 104 is in use. For example, the maximum temperature the adhesive member 302a is expected to receive when the radiation detection apparatus 104 is in use is 60° C. in this example. In this case, the temperature for lowering the adhesive force of the adhesive member 302a may be a temperature higher than 60° C. such as 70° C. or higher, for example.

Examples of a substance for lowering the adhesive force by adding water include acrylic-based substances. When lowering the adhesive force of the adhesive member 302a by adding water, the repair worker may drop a small amount of water on the adhesive member 302a.

Examples of a substance for lowering the adhesive force by dropping a solution include acrylic-based substances. When lowering the adhesive force of the adhesive member 302a by dropping a solution, the repair worker may drop a specific solution (for example, isopropyl alcohol, acetone, or the like) for lowering the adhesive force of the adhesive member 302a on the adhesive member 302a.

Examples of a substance for lowering the adhesive force via photostimulation include epoxy-based substances. When lowering the adhesive force of the adhesive member 302a via photostimulation, the repair worker may irradiate the adhesive member 302a with light (for example, ultraviolet light or the like) of a specific wavelength.

As illustrated in FIG. 3A, the adhesive member 302a and the adhesive member 302b may be separate from one another. This makes it easier to apply a stimulation to the adhesive member 302a individually (in other words, not affecting the adhesive member 302b). The adhesive force of the adhesive member 302a and the adhesive force of the adhesive member 302b may be lowered using the same stimulation or may be lowered using different stimulations. When the adhesive force of the adhesive member 302a and the adhesive force of the adhesive member 302b are lowered using different stimulations, it is easier to apply a stimulation to the adhesive member 302a individually (in other words, not affecting the adhesive member 302b).

The stimulation for lowering the adhesive force of the adhesive member 302a and the adhesive force of the adhesive member 302b may be different types of stimulation. For example, the adhesive force of the adhesive member 302a may be lowered via heating, and the adhesive force of the adhesive member 302b may be lowered by adding water. The stimulation for lowering the adhesive force of the adhesive member 302a and the adhesive force of the adhesive member 302b may be the same type of stimulation but at different strengths. For example, the adhesive force of the adhesive member 302a may be lowered via heating at 70° C., and the adhesive force of the adhesive member 302b may be lowered via heating at 80° C. When the entire sensor unit 300 is heated, the adhesive force of only the adhesive member 302a is lowered via heating at 70° C., but the adhesive force of both the adhesive member 302a and the adhesive member 302b are lowered via heating at 80° C. The adhesive force of either one of the adhesive members 302a and 302b may be lowered by a stimulation of a low strength. Of the sensor panels 301a to 301c, the sensor panel 301a located close to the outside of the radiation detection apparatus 104 can be considered the easiest to be damaged by an impact or the like. Thus, of the adhesive members 302a and 302b, the adhesive force of the adhesive member 302a located close to the outside of the radiation detection apparatus 104 may be lowered by a stimulation of a lower strength. This makes it easier to individually separate the sensor panel 301a.

In the example illustrated in FIG. 3B, the sensor module 202 may include a sensor unit 310, a frame 303, and a circuit board 304. The sensor unit 310 may include a plurality of sensor panels 311a to 311c and a plurality of adhesive members 312a and 312b. Hereinafter, the plurality of sensor panels 311a to 311c are referred to by the generic term sensor panel 311. The description of the sensor panel 311 may be applied to each one of the plurality of sensor panels 311a to 311c. Also, the adhesive members 312a and 312b are referred to by the generic term adhesive member 312. The description of the adhesive member 312 may be applied to each one of the plurality of adhesive members 312a and 312b. In the example in FIG. 3B, one sensor module 202 includes three sensor panels 311a to 311c, but the number of sensor panels is to limited by this example. Also, one sensor module 202 may include a plurality of the sensor units 310.

The plurality of sensor panels 311a to 311c each generate a signal in accordance with incident radiation. The plurality of sensor panels 311a to 311c are arranged side by side with respect to the radiation 121. The plurality of sensor panels 311a to 311c being arranged side by side with respect to the radiation 121 means that the plurality of sensor panels 311a to 311c do not overlap in the advancement direction of the radiation 121. As described below, the sensor panel 311 may include a plurality of pixels arranged along a flat surface (for example, the upper surface of the sensor panel 311) orthogonal to the advancement direction of the radiation 121.

The adhesive member 312a is located between the sensor panel 311a and the sensor panel 311b. The adhesive member 312a is in contact with both the side surface of the sensor panel 311a and the side surface of the sensor panel 311b and thus couples together the sensor panels. The adhesive member 312b is located between the sensor panel 311b and the sensor panel 311c. The adhesive member 312b is in contact with both the side surface of the sensor panel 311b and the side surface of the sensor panel 311c and thus couples together the sensor panels. The thickness of the sensor panel 311 may range from 1.7 mm to 6.6 mm, for example. The thickness of the adhesive member 312 may range from 0.01 mm to 10 mm, for example.

The sensor panel 311 and the circuit board 304 are connected by a (non-illustrated) cable (flexible cable, for example). The signal generated at the sensor panel 311 is read out to the DAS 108 via the circuit board 304. The description of the frame 303 and the circuit board 304 may be similar to the description using FIG. 3A. The sensor unit 310 may be mechanically fixed to the frame 303 using a fastener such as a machine screw or the like.

The characteristics of the adhesive members 312a and 312b may be similar to the characteristics of the adhesive member 302a described above in regard to the sensor unit 300. The relationship between the adhesive member 312a and the adhesive member 312b may be similar to the relationship between the adhesive member 302a and the adhesive member 302b described above in regard to the sensor unit 300. The sensor panel without an abnormality in the sensor unit 310 can also be reused.

The adhesive member 312 of the sensor unit 310 may include a radiation absorbing member. This allows radiation between adjacent sensor panels 311 in the sensor unit 310 to be reduced. For example, a portion of the radiation that is incident on the upper surface of the sensor panel 311a at an angle may escape through the side surface of the sensor panel 311a and travel toward the sensor panel 311b. By including a radiation absorbing member in the adhesive member 312b, such radiation can be suppressed from reaching the sensor panel 311b.

In the example illustrated in FIG. 3C, the sensor module 202 may include a sensor unit 320, a frame 303, and a circuit board 304. The sensor unit 320 may include a plurality of sensor panels 321a to 321c and a plurality of adhesive members 322a and 322b. Hereinafter, the plurality of sensor panels 321a to 321c are referred to by the generic term sensor panel 321. The description of the sensor panel 321 may be applied to each one of the plurality of sensor panels 321a to 321c. Also, the adhesive members 322a and 322b are referred to by the generic term adhesive member 322. The description of the adhesive member 322 may be applied to each one of the plurality of adhesive members 322a and 322b. In the example in FIG. 3C, one sensor module 202 includes three sensor panels 321a to 321c, but the number of sensor panels is to limited by this example. Also, one sensor module 202 may include a plurality of the sensor units 320.

The plurality of sensor panels 321a to 321c each generate a signal in accordance with incident radiation. The plurality of sensor panels 321a to 321c are arranged side by side with respect to the radiation 121. The plurality of sensor panels 321a to 321c being arranged side by side with respect to the radiation 121 means that the plurality of sensor panels 301a to 301c do not overlap in the advancement direction of the radiation 121. As described below, the sensor panel 321 may include a plurality of pixels arranged along a flat surface (for example, the larger side surface of the sensor panel 321) parallel with the advancement direction of the radiation 121.

The adhesive member 322a is located between the sensor panel 321a and the sensor panel 321b. The adhesive member 322a is in contact with both the side surface of the sensor panel 321a and the side surface of the sensor panel 321b and thus couples together the sensor panels. The adhesive member 322b is located between the sensor panel 321b and the sensor panel 321c. The adhesive member 322b is in contact with both the side surface of the sensor panel 321b and the side surface of the sensor panel 321c and thus couples together the sensor panels. The thickness of the sensor panel 321 may range from 1.7 mm to 6.6 mm, for example. The thickness of the adhesive member 322 may range from 0.01 mm to 10 mm, for example.

The sensor panel 321 and the circuit board 304 are connected by a (non-illustrated) cable (flexible cable, for example). The signal generated at the sensor panel 321 is read out to the DAS 108 via the circuit board 304. The description of the frame 303 and the circuit board 304 may be similar to the description using FIG. 3A. The sensor unit 320 may be mechanically fixed to the frame 303 using a fastener such as a machine screw or the like.

The characteristics of the adhesive members 322a and 322b may be similar to the characteristics of the adhesive member 302a described above in regard to the sensor unit 300. The relationship between the adhesive member 322a and the adhesive member 322b may be similar to the relationship between the adhesive member 302a and the adhesive member 302b described above in regard to the sensor unit 300. The sensor panel without an abnormality in the sensor unit 320 can also be reused.

The adhesive member 322 of the sensor unit 320 may include a radiation absorbing member. This allows radiation between adjacent sensor panels 321 in the sensor unit 320 to be reduced. For example, a portion of the radiation that is incident on the upper surface of the sensor panel 321a at an angle may escape through the side surface of the sensor panel 321a and travel toward the sensor panel 321b. By including a radiation absorbing member in the adhesive member 322b, such radiation can be suppressed from reaching the sensor panel 321b.

Examples of sensor panels that can be used as any one of the sensor panels 301a to 301c in FIG. 3A and any one of the sensor panels 311a to 311c in FIG. 3B will now be described with reference to the cross-sectional views of FIGS. 4A to 4D. FIGS. 4A to 4D are cross-sectional views taken along a plane perpendicular to the advancement direction of the radiation 121. In one radiation detection apparatus 104, sensor panels of the same configuration may be used, or sensor panels with different configurations may be used. The sensor panels 301a to 301c in FIG. 3A and the sensor panels 311a to 311c in FIG. 3B may have a known configuration. Thus, the configuration of a representative sensor panel will be described below. For the portions that are not described in detail, a known configuration may be used.

Figure 4A:
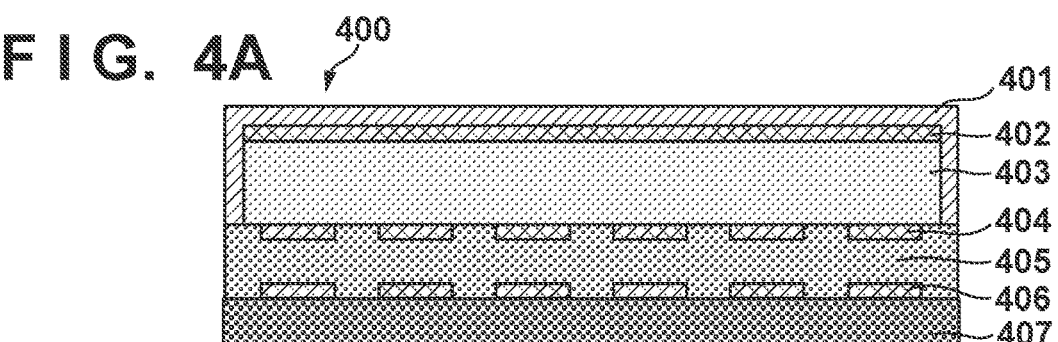
FIGS. 4A to 4D are cross-sectional views for describing example configurations of sensor panels according to some embodiments.

A sensor panel 400 illustrated in FIG. 4A may include a protective layer 401, a shared electrode 402, a semiconductor layer 403, pixel electrodes 404, an adhesive member 405, a circuit electrode 406, and a counting circuit 407. The semiconductor layer 403 converts radiation into a charge. The semiconductor layer 403 may be a single-crystal substrate of a semiconductor that converts radiation into a direct charge such as cadmium zinc telluride (CdZnTe) or cadmium telluride (CdTe). The semiconductor layer 403 may be a single-crystal substrate of a semiconductor such as silicon (Si), lead iodide (PbI$_2$), mercury iodide (HgI$_2$), bismuth iodide (BiI$_3$), and thallium bromide (TlBr).

The shared electrode 402 is formed on the upper surface of the semiconductor layer 403. The shared electrode 402 may be made of a metal such as aluminum, for example. The shared electrode 402 is used to apply a voltage to the semiconductor layer 403. The pixel electrode 404 is formed on the lower surface of the semiconductor layer 403. For one semiconductor layer 403, a plurality of the pixel electrodes 404 are formed. A signal in accordance with the charge generated at the corresponding position of the semiconductor layer 403 is read out from each pixel electrode 404. In this manner, one pixel electrode 404 corresponds to one pixel. The protective layer 401 covers the upper surface of the shared electrode 402, the side surfaces of the shared electrode 402, and the side surfaces of the semiconductor layer 403. The protective layer 401 may be made of parylene or the like, for example.

The counting circuit 407 may be energy-resolving counting electronics (ERCE) for counting the charges generated at the semiconductor layer 403. For example, the counting circuit 407 may include a function for counting electric pulses generated when a radiation photon is incident on the semiconductor layer 403. In this manner, the sensor panel 400 can operate as a photon counting sensor panel. Alternatively, the counting circuit 407 may read out the voltage in accordance with the charge accumulated in the semiconductor layer 403 from the semiconductor layer 403.

The circuit electrode 406 is formed on the upper surface of the counting circuit 407. For one counting circuit 407, a plurality of the circuit electrodes 406 are formed. The adhesive member 405 couples together the semiconductor layer 403 and the counting circuit 407. The adhesive member 405 may have electrical conductivity and be an anisotropic conductive film (ACF), for example. By the adhesive member 405 having electrical conductivity, the individual pixel electrodes 404 and the individual circuit electrodes 406 are electrically connected.

The sensor panel 400 may further include an interposer between the semiconductor layer 403 and the counting circuit 407. An application specific integrated circuit (ASIC) may be used instead of the energy-resolving counting electronics.

When the sensor panel 400 is used in the sensor unit 300, the adhesive force of the adhesive member 405 may not be lowered via a stimulation for lowering the adhesive force of the adhesive member 302. Accordingly, even when the adhesive force of the adhesive member 302 is lowered, the couple between the semiconductor layer 403 and the counting circuit 407 is retained. The adhesive force of the adhesive member 405 may not be lowered via a stimulation. Alternatively, the adhesive force of the adhesive member 405 may be lowered via a stimulation different from the stimulation for lowering the adhesive force of the adhesive member 302. This also holds when the sensor panel 400 is used in the sensor unit 310.

Figure 4B:
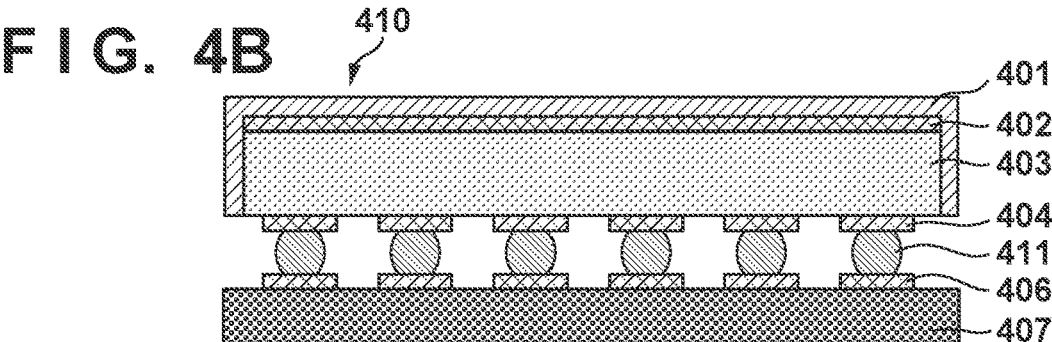

The sensor panel 410 illustrated in FIG. 4B may be similar to the sensor panel 400 except that the sensor panel 410 includes bumps 411 instead of the adhesive member 405. The bumps 411 electrically and physically connects the pixel electrode 404 and the circuit electrode 406. The bumps 411 may be formed via soldering, for example. The sensor panel 410 can also operate as a photon counting sensor panel. The sensor panel 410 does not include an adhesive member.

Figure 4C:
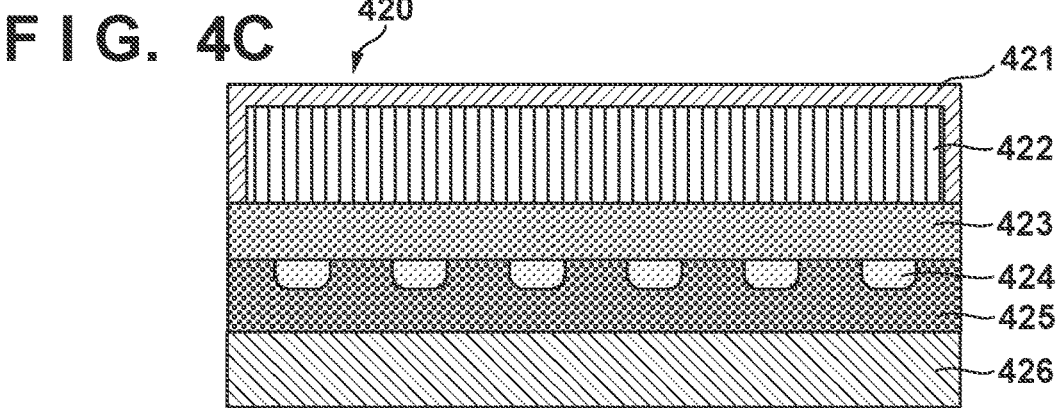

A sensor panel 420 illustrated in FIG. 4C may include a protective layer 421, a scintillator layer 422, an adhesive member 423, a sensor layer 425, and a base 426. The scintillator layer 422 converts incident radiation into light.

The protective layer 421 covers the upper surface and the side surfaces of the scintillator layer 422. The protective layer 401 may be made of aluminum or the like, for example.

The sensor layer 425 generates a signal in accordance with the light generated at the scintillator layer 422. The sensor layer 425 may include a photoelectric conversion unit 424 that converts light generated at the scintillator 422 into a charge. For one sensor layer 425, a plurality of the photoelectric conversion units 424 are formed. A signal in accordance with the light converted from radiation is read out above the photoelectric conversion unit 424. Accordingly, one photoelectric conversion unit 424 corresponds to one pixel. The adhesive member 423 couples together the scintillator layer 422 and the sensor layer 425.

When the sensor panel 420 is used in the sensor unit 300, the adhesive force of the adhesive member 423 may not be lowered via a stimulation for lowering the adhesive force of the adhesive member 302. Accordingly, even when the adhesive force of the adhesive member 302 is lowered, the couple between the semiconductor layer 403 and the counting circuit 407 is retained. The adhesive force of the adhesive member 423 may not be lowered via a stimulation. Alternatively, the adhesive force of the adhesive member 423 may be lowered via a stimulation different from the stimulation for lowering the adhesive force of the adhesive member 302. This also holds when the sensor panel 420 is used in the sensor unit 310.

When the sensor panel 420 is used in the sensor unit 300, the adhesive member 302 may have light shielding characteristics higher than that of the adhesive member 423. Since the light generated at the scintillator layer 422 reaches the sensor layer 425 through the adhesive member 423, the higher the transmittance of the adhesive member 423 the better. On the other hand, when the light generated at the scintillator layer 422 of one sensor panel 301 (for example, the sensor panel 301a) reaches another sensor panel 301 (for example, the sensor panel 301b), the energy level resolving accuracy is reduced. Accordingly, the light shielding characteristics of the adhesive member 302 (for example, the adhesive member 302b) may be high. This also holds when the sensor panel 420 is used in the sensor unit 310.

Figure 4D:
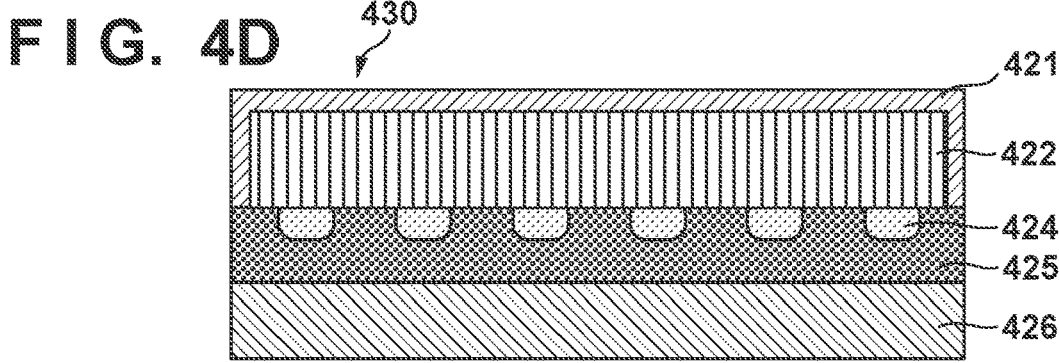

The sensor panel 430 illustrated in FIG. 4D may be similar to the sensor panel 420 except that the sensor panel 430 does not include the adhesive member 423. Such a configuration may be formed via vapor deposition of a scintillator on the sensor layer.

Figure 5:
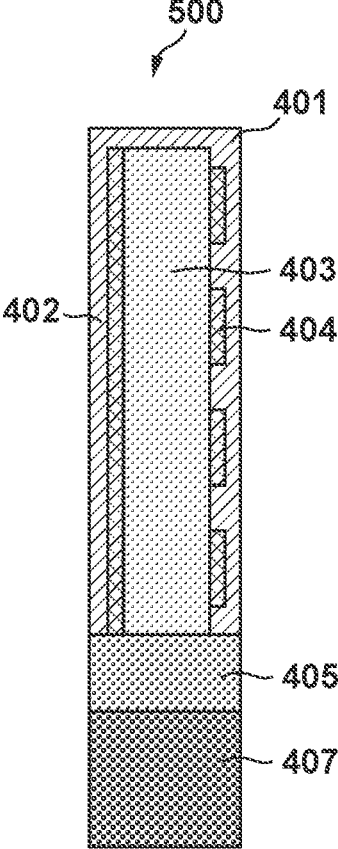
FIG. 5 is a cross-sectional view for describing an example configuration of a sensor panel according to some embodiments.

An example of a sensor panel that can be used as any one of the sensor panels 321a to 321c in FIG. 3C will now be described with reference to the cross-sectional view of FIG. 5. FIG. 5 is a cross-sectional view taken along a plane parallel with the advancement direction of the radiation 121. The sensor panels 321a to 321c in FIG. 3C may have a known configuration. Thus, the configuration of a representative sensor panel will be described below. For the portions that are not described in detail, a known configuration may be used.

A sensor panel 500 illustrated in FIG. 5 may include the protective layer 401, the shared electrode 402, the semiconductor layer 403, the pixel electrode 404, the adhesive member 405, and the counting circuit 407. The components may include functions similar to the components of the sensor panel 400.

In the sensor panel 500, the shared electrode 402, the semiconductor layer 403, and the pixel electrode 404 have been rotated 90 degrees from that in the sensor panel 400. Accordingly, the shared electrode 402 is formed on one side surface (left side surface in FIG. 5) of the semiconductor layer 403, and the pixel electrode 404 is formed on the other side surface (right side surface in FIG. 5) of the semiconductor layer 403. The radiation 121 enters from the upper surface of the sensor panel 400. In other words, the sensor panel 500 is orientated so that the radiation 121 incident on the radiation detection apparatus 104 is emitted at the surface (surface on the upper side in FIG. 5) that intersects the surface (surface on the right side in FIG. 5) where the pixel electrodes 404 of the sensor panel 500 are disposed. The adhesive member 405 couples together the semiconductor layer 403 (specifically, the lower surface thereof) and the counting circuit 407 (specifically, the upper surface thereof).

The radiation that enters from the upper surface of the sensor panel 500 is converted into a charge at a depth in accordance with the energy level, and the charge is read out from an individual pixel electrode 404. In this manner, the counting circuit 407 can count the number of photons for each energy level.

Arrangement examples of the adhesive member 302a that couples together the two sensor panels 301a and 301b will be described with reference to FIGS. 6A to 6E. The following description may also be applied to the other adhesive members 302b, 312a to 312c, and 322a to 322c. FIGS. 6A to 6D are diagrams of the sensor unit 300 as seen from the lateral direction (in other words, the direction orthogonal to the advancement direction of the radiation 121).

Figure 6A:
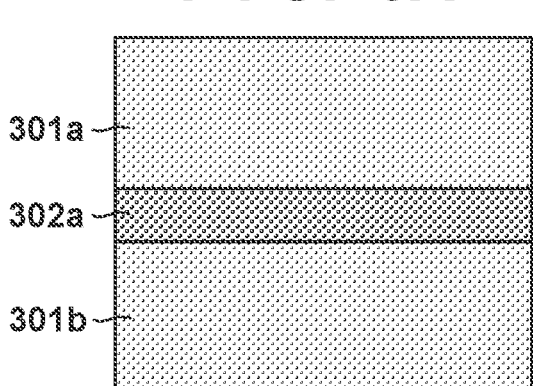
FIGS. 6A to 6E are cross-sectional views for describing arrangement examples of adhesive members according to some embodiments.

In the example illustrated in FIG. 6A, the adhesive member 302a is located between the sensor panel 301a and the sensor panel 301b. The adhesive member 302a is in contact with the entire lower surface of the sensor panel 301a and in contact with the entire upper surface of the sensor panel 301b.

Figure 6B:
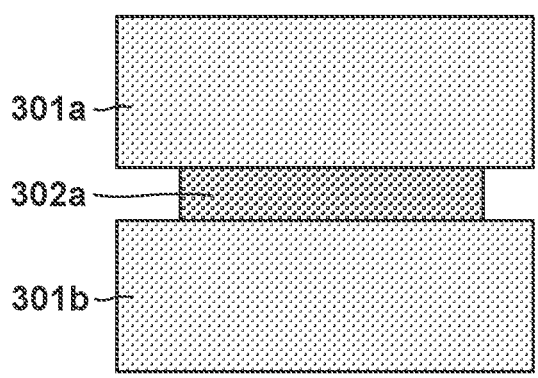

In the example illustrated in FIG. 6B, the adhesive member 302a is located between the sensor panel 301a and the sensor panel 301b. The adhesive member 302a is in contact with only a portion of the lower surface of the sensor panel 301a and in contact with only a portion of the upper surface of the sensor panel 301b. According to this arrangement, a stimulation is easily applied to the adhesive member 302a.

Figure 6C:
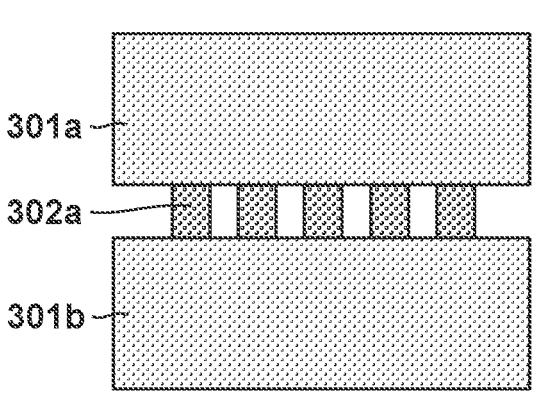

In the example illustrated in FIG. 6C, the adhesive member 302a is located between the sensor panel 301a and the sensor panel 301b. The adhesive member 302a is in contact with only a portion of the lower surface of the sensor panel 301a and in contact with only a portion of the upper surface of the sensor panel 301b. The adhesive member 302a is divided into a plurality of portions.

Figure 6D:
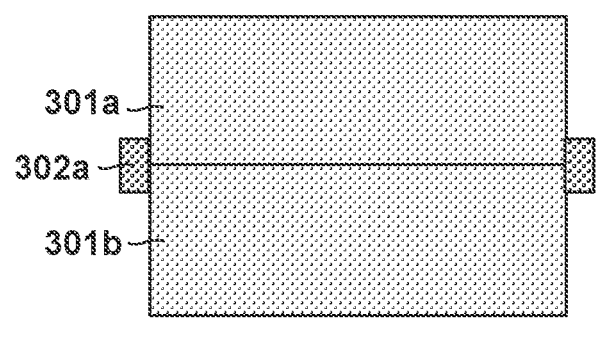
Figure 6E:
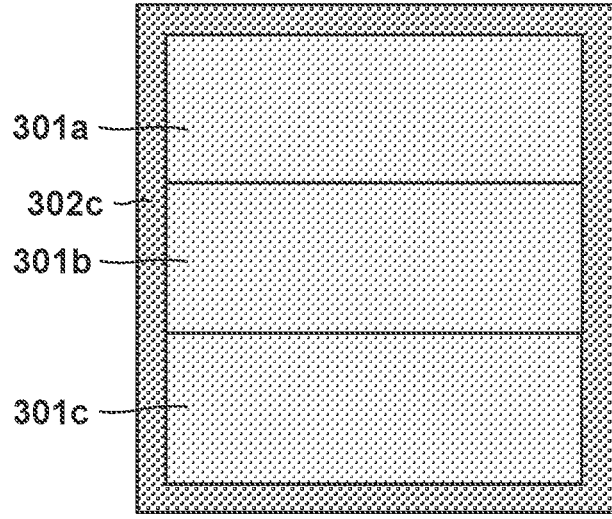

In the example illustrated in FIG. 6D, the sensor panel 301a (specifically, the lower surface thereof) and the sensor panel 301b (specifically, the upper surface) are coupled together. The adhesive member 302a covers the boundary between the sensor panel 301a and the sensor panel 301b from the side. The adhesive member 302a may partially cover the boundary or may completely cover the boundary. According to this arrangement, a stimulation is easily applied to the adhesive member 302a. Also, since the distance between the sensor panel 301a and the sensor panel 301b can be reduced, the thickness of the radiation detection apparatus 104 can be reduced.

In the example illustrated in FIG. 6D, the adhesive members 302a and 302b are integrally formed as an adhesive member 302c. The sensor panel 301a (specifically, the lower surface thereof) and the sensor panel 301b (specifically, the upper surface) are coupled together. The sensor panel 301b (specifically, the lower surface thereof) and the sensor panel 301c (specifically, the upper surface) are coupled together. The adhesive member 302c covers the sensor panels 301a to 301c as a whole.

Arrangement examples of the adhesive member 302a that couples together the two sensor panels 301a and 301b will be described with reference to FIGS. 7A to 7E. The following description may also be applied to the other adhesive members 302b, 312a to 312c, and 322a to 322c. FIGS. 6A to 6D illustrate the surfaces of the sensor panel 301a that are coupled by the adhesive member 302a. In any of the following examples, the surface of the sensor panel 301a that faces the sensor panel 301b includes a portion in contact with the adhesive member 302a and a portion not in contact with the adhesive member 302a.

In the example illustrated in FIG. 7A, the adhesive member 302a is divided into a plurality of linear portions that are coupled to the surface of the sensor panel 301a in a striped pattern. In the example illustrated in FIG. 7B, the adhesive member 302a is a single member that is coupled only to the central portion of the surface of the sensor panel 301a. In the example illustrated in FIG. 7C, the adhesive member 302a is divided into a plurality of portions that are coupled to the surface of the sensor panel 301a at points over the entire surface. In the example illustrated in FIG. 7D, the adhesive member 302a is divided into a plurality of portions that are coupled to the surface of the sensor panel 301a at the four corners. In the example illustrated in FIG. 7E, the adhesive member 302a is a single member that is coupled only to the peripheral portion of the surface of the sensor panel 301a.

In the embodiments described above, the radiation detection apparatus 104 has been described in the context of the CT apparatus 100. However, alternatively, the radiation detection apparatus 104 may be used in another apparatus such as a fluoroscopic examination apparatus, an article inspection apparatus, a radiation image sensor, a flat panel detector (FPD), and the like. Also, in the embodiments described above, the radiation detection apparatus 104 that detects radiation has been described. However, the embodiments are not limited thereto, and, for example, the embodiments described above are applicable to a radiation detector that detects γ-rays, particle radiation, and the like. Also, other than the CT apparatus 100, the embodiments described above are also applicable to a radiation examination apparatus including the radiation detection apparatus 104. In such a case, the radiation examination apparatus, for example, includes a Positron Emission Tomography (PET) apparatus, a Single Photon Emission Computer Tomography (SPECT) apparatus, or the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2022-175026, filed Oct. 31, 2022, which is hereby incorporated by reference herein in its entirety.

What is claimed is:

1. A radiation detection apparatus, comprising:
   a first sensor panel configured to generate a signal in accordance with incident radiation;
   a second sensor panel configured to generate a signal in accordance with incident radiation;
   a third sensor panel configured to generate a signal in accordance with incident radiation;

a first adhesive member that couples together the first sensor panel and the second sensor panel; and
   a second adhesive member that couples together the first sensor panel or the second sensor panel, and the third sensor panel, wherein
   the first adhesive member and the second adhesive member are separated from one another,
   a stimulation for lowering an adhesive force of the first adhesive member and a stimulation for lowering an adhesive force of the second adhesive member are different from one another, and
   when a stimulation is applied to the first adhesive member, an adhesive force of the first adhesive member is lowered to a strength at which the first sensor panel and the second sensor panel can be separated without causing damage.

2. The radiation detection apparatus according to claim 1, wherein the first sensor panel includes a semiconductor layer configured to convert radiation into a charge and a counting circuit configured to count the charge.

3. The radiation detection apparatus according to claim 2, wherein the first sensor panel further includes a third adhesive member that couples together the semiconductor layer and the counting circuit, and
   an adhesive force of the third adhesive member is not lowered by a stimulation for lowering an adhesive force of the first adhesive member.

4. The radiation detection apparatus according to claim 1, wherein the first sensor panel includes a scintillator layer configured to convert that converts radiation into light, and a sensor layer including a photoelectric conversion unit configured to convert light generated at the scintillator layer into a charge.

5. The radiation detection apparatus according to claim 4, wherein the first sensor panel further includes a fourth adhesive member that couples together the scintillator layer and the sensor layer, and
   an adhesive force of the fourth adhesive member is not lowered by a stimulation for lowering an adhesive force of the first adhesive member.

6. The radiation detection apparatus according to claim 5, wherein the first adhesive member has higher light shielding characteristics than the fourth adhesive member.

7. The radiation detection apparatus according to claim 1, wherein the first sensor panel and the second sensor panel are layered on one another with respect to radiation incident on the radiation detection apparatus.

8. The radiation detection apparatus according to claim 7, wherein the first adhesive member is located between the first sensor panel and the second sensor panel, and
   a surface of the first sensor panel facing the second sensor panel includes a first portion in contact with the first adhesive member and a second portion that is not in contact with the first adhesive member.

9. The radiation detection apparatus according to claim 7, wherein the first sensor panel and the second sensor panel contact each other, and
   the first adhesive member covers a boundary between the first sensor panel and the second sensor panel.

10. The radiation detection apparatus according to claim 1, wherein the first sensor panel and the second sensor panel are arranged side by side with respect to radiation incident on the radiation detection apparatus.

11. The radiation detection apparatus according to claim 1, wherein each of the first sensor panel and the second sensor panel is orientated so that radiation incident on the radiation detection apparatus is emitted at a surface that intersects a surface where pixel electrodes of each sensor panel is disposed, and the first adhesive member includes a radiation absorbing member.

12. The radiation detection apparatus according to claim 1, wherein the stimulation includes at least one of heating, adding water, dropping a solution or photostimulation.

13. A CT apparatus, comprising:

the radiation detection apparatus according to claim 1;

a radiation generator configured to emit radiation toward the radiation detection apparatus; and a signal processing unit configured to process signals output from the radiation detection apparatus.

14. The CT apparatus according to claim 13, wherein the radiation detection apparatus is a photon counting radiation detection apparatus, and the signal processing unit is configured to generate image data using a counting result of radiation photons resulting from radiation that has passed through an inspection subject.

15. A radiation detection apparatus, comprising:

a first sensor panel configured to generate a signal in accordance with incident radiation;

a second sensor panel configured to generate a signal in accordance with incident radiation;

a third sensor panel configured to generate a signal in accordance with incident radiation;

a first adhesive member that couples together the first sensor panel and the second sensor panel; and a second adhesive member that couples together the first sensor panel or the second sensor panel, and the third sensor panel, wherein the first adhesive member and the second adhesive member are separated from one another, a stimulation for lowering an adhesive force of the first adhesive member and a stimulation for lowering an adhesive force of the second adhesive member are different from one another, and the first sensor panel and the second sensor panel are configured to separate by a stimulation applied to the first adhesive member.

16. A sensor module, comprising:

a first sensor panel configured to generate a signal in accordance with incident radiation;

a second sensor panel configured to generate a signal in accordance with incident radiation;

a third sensor panel configured to generate a signal in accordance with incident radiation;

first adhesive member that couples together the first sensor panel and the second sensor panel; and a second adhesive member that couples together the first sensor panel or the second sensor panel, and the third sensor panel, wherein the first adhesive member and the second adhesive member are separated from one another, a stimulation for lowering an adhesive force of the first adhesive member and a stimulation for lowering an adhesive force of the second adhesive member are different from one another, and the first sensor panel and the second sensor panel are configured to separate by a stimulation applied to the first adhesive member.

* * * * *